United States Patent [19]

Kawai et al.

[11] 4,125,372
[45] Nov. 14, 1978

[54] METHOD AND DEVICE FOR TESTING LIQUIDS

[75] Inventors: Shoji Kawai, Kyoto; Shigeki Yamada; Shinichi Kishimoto, both of Uji, all of Japan

[73] Assignee: Kabushiki Kaisha Kyoto Kaiichi Kagaku, Japan

[21] Appl. No.: 668,745

[22] Filed: Mar. 19, 1976

[30] Foreign Application Priority Data

Apr. 1, 1975 [JP] Japan .................................. 50-40007

[51] Int. Cl.² .................... G01N 21/06; G01N 21/20; G01N 31/22; G01N 33/16
[52] U.S. Cl. .................................. 23/230 B; 422/56; 422/57
[58] Field of Search ....................... 23/230 B, 253 TP

[56] References Cited

U.S. PATENT DOCUMENTS

| 3,901,657 | 8/1975 | Lightfoot | 23/253 TP |
|---|---|---|---|
| 3,932,132 | 1/1976 | Hijikata | 23/253 TP X |
| 3,932,133 | 1/1976 | Ishikawa | 23/253 TP X |
| 3,941,876 | 3/1976 | Marinkovich | 23/253 TP X |
| 3,963,442 | 6/1976 | Bullard | 23/253 TP |
| 3,973,129 | 8/1976 | Blumberg | 23/230 B X |

Primary Examiner—Sidney Marantz
Attorney, Agent, or Firm—Steinberg & Blake

[57] ABSTRACT

A method and device for testing a liquid such as urine for obtaining at least qualitative, but also quantitative, if desired, information in connection with a substance which may be present in the liquid. A reference body and at least one test body are dipped into and removed from the liquid which is to be tested, a suitable means being connected with the bodies to facilitate the dipping thereof into and the removal thereof from the liquid. The test body is capable of giving a color indication in connection with the substance while the reference body has characteristics substantially identical with those of the test cody except that the reference body is incapable of giving a color indication in connection with the substance. Thus, after removal of the bodies from the liquid the reflectivities thereof may be compared so as to give at least a qualitative, but also a quantitative, if desired, indication of the substance in connection with the liquid which is tested.

12 Claims, 5 Drawing Figures

U.S. Patent  Nov. 14, 1978  Sheet 1 of 2  4,125,372
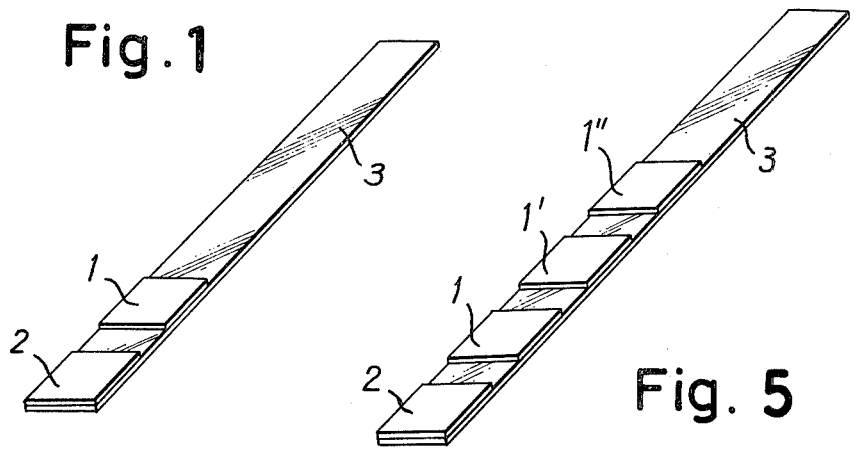
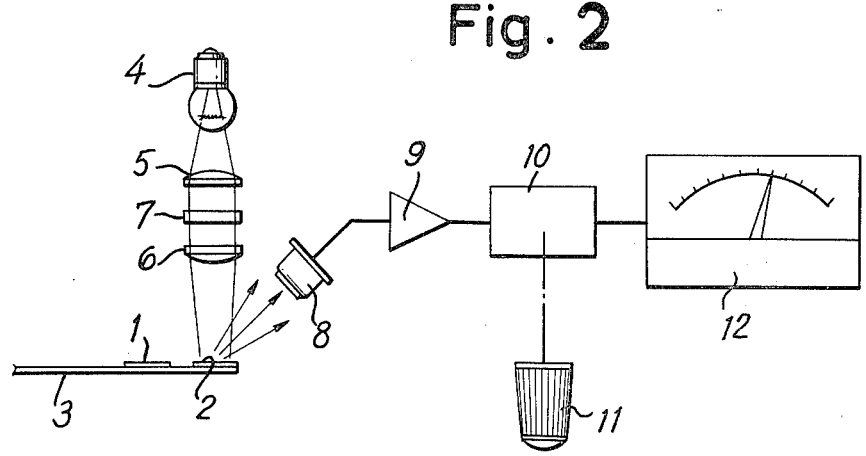

METHOD AND DEVICE FOR TESTING LIQUIDS

BACKGROUND OF THE INVENTION

The present invention relates to the testing of liquid specimens such as urine and the like.

In general, examination of a liquid such as urine is carried out with the use of color reaction test papers. At the present time test methods utilizing color reaction test papers are highly qualitative. Thus, in the strict sense, the known methods and devices will give an indication only as to whether or not the suspected constituent or substance is present or not present in the liquid such as urine. The primary reason for utilizing color reaction test paper so frequently, from among the various types of analyzing means which are available, is, in addition to its simplicity, the fact that the primary object of examining a liquid such as urine is to detect the presence or absence of abnormal substances such as glucose, protein, ect. which normally will not be encountered in the urine of a healthy individual. Clinically, the desired objective is almost entirely achieved simply by judging whether or not such substances are present or absent in the urin or other liquid which is tested.

This reason, however, is in itself not sufficient for entirely supporting the present conditions of use of color reaction papers. Many urine samples which have been judged to give a positive or quasi-positive result after examination require further quantitative examination. Thus, these samples are further examined by quantitative analyzing means such as colorimetric analysis. For this reason it is a well known fact that clinical physicians are not satisfied only with the result of color reaction test paper examination.

In addition, many specialists are doubtful of the ability of color reaction test paper to give a proper indication of the presence or absence of abnormal substances. Thus, it is well known that the capability of achieving a purely qualitative result is unreliable.

In this connection the following example may be considered:

It is well known that a pronounced coloring of the urine itself due to consumption of vitamin compounds by the individual or due to presence of bilirubin will cause errors in measurement. Due to the coloring of the urine itself from such causes, which are given only by way of example, as well as various other causes, it sometimes happens that the individual judging the test paper overlooks slight coloring of the color reaction test paper or believes that a detection has been made of a given substance by way of the color reaction test paper whereas actually the substance is not present and a false judgment has been made. Thus, with conventional color reaction test papers, the individual examining the test paper cannot always correctly judge the presence or absence of abnormal substances and there is a considerable possibility of erroneous judgment. Such erroneous judgment due to overlapping or confusion of the color of the urine itself and the color reaction represents a serious technical drawback which is inevitable when utilizing color reaction test paper.

In order to achieve an accurate measurement it is necessary to use, instead of the unaided eye type of observation, spectral reflection measurement, with high-quality optical instruments being provided for this purpose. With methods of this type also, however, it is difficult to obtain entirely satisfactory results inasmuch as the spectral reflectivity of the color reaction test paper is observed under conditions where there is still an overlap or confusion between the color reaction due to reaction of the reagent in the test paper with the abnormal substance and due to coloring resulting from the colored constituents of the urine itself, as distinct from the substance the presence of which in the urine is to be tested.

SUMMARY OF THE INVENTION

It is accordingly a primary object of the present invention to provide a method and apparatus which will avoid these drawbacks.

In particular, it is an object of the present invention to provide a method and apparatus capable of utilizing accurate color reaction measuring techniques with optical instruments for carrying out spectral reflectivity measurements while utilizing in addition certain advantageous techniques.

Thus, it is an object of the present invention to provide by way of color reaction test paper not only an analysis with respect to detecting the presence or absence of an abnormal substance but also an analysis which will give a quantitative measurement value.

Thus, it is an object of the present invention to provide a simple, convenient, and highly accurate and effective method and device for giving in connection with a substance in a liquid at least a qualitative indication and in addition a quantitative indication, if desired.

According to the invention there are at least a pair of bodies one of which is a test body and the other of which is a reference body. These bodies have substantially identical characteristics with respect to liquid which is to be tested, except that the test body has the capability of giving a color indication in connection with a given substance whereas the reference body does not have this capability. A means is connected with these bodies to facilitate dipping thereof into and removal thereof from a liquid which is to be tested. By comparing the color difference, if any, between the bodies after they are removed from the liquid it is possible to achieve the desired information.

BRIEF DESCRIPTION OF DRAWINGS

The invention is illustrated by way of example in the accompanying drawings which form part of this application and in which:

FIG. 1 is a perspective illustration of one embodiment of a structure forming at least part of a device of the invention.

FIG. 2 is a schematic representation of an optical means to be used with the structure of FIG. 1;

FIG. 5 is a perspective view of another embodiment of a structure which will form at least part of the device of the invention.

DESCRIPTION OF PREFERRED EMBODIMENTS

Figure 3:
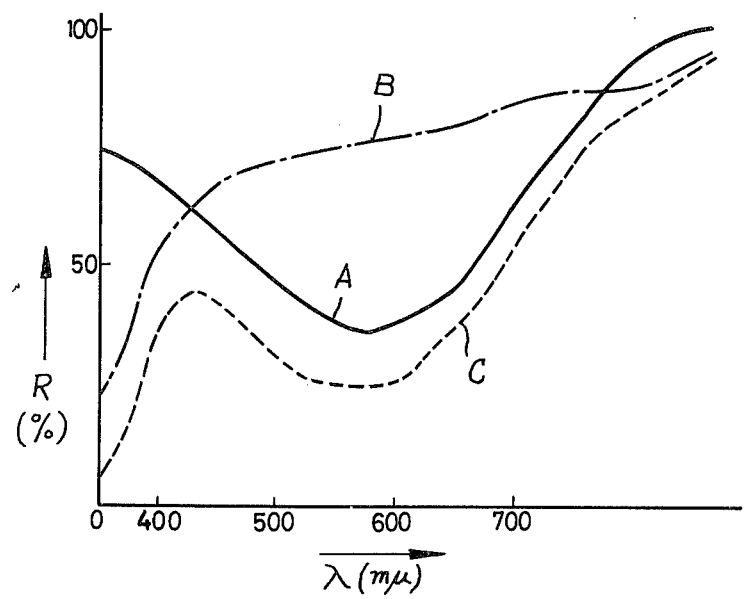
FIG. 3 is a graph illustrating spectral reflectivity characteristic curves of color reaction test paper pieces.

Referring to FIG. 1, there is illustrated therein a structure which forms at least part of the device of the invention. However, as will be apparent from the description below, the invention is not restricted to what is shown in FIG. 1.

The structure illustrated in FIG. 1 includes a test body 1 in the form of a color reaction test paper piece capable of reacting, for example, with glucose, protein, etc. when dipped into a urine specimen, the color-reaction test body 1 providing a coloring the intensity of which corresponds to the concentration of substances of the latter type when they are present in the tested liquid. This color reaction test paper piece 1 is generally produced by impregnating a white filter paper piece with a reagent which provides a given color as a result of a selected reaction with the glucose or other substance for which the test is made, the coloring having in the test paper piece a constant density.

A reflectivity reference or compensation piece 2 is also made of a filter paper which may be the same as that used for the test body 1 and which is of the same configuration as the color reaction test paper piece 1. The color reaction test paper piece 1 and the reflectivity reference or compensation piece 2 are connected with a means to facilitate the dipping thereof into and the removal thereof from the liquid specimen. Thus FIG. 1 shows an elongated strip 3 made of a suitable plastic, for example, and carrying the bodies 1 and 2 in the manner illustrated in FIG. 1, these bodies 1 and 2 being fastened to the strip 3 as by being adhered thereto with a material which is neutral with respect to the liquid and components thereof. Thus, the individual who uses the device simply holds the strip 3 with his fingers and dips both the color reaction test paper body 1 and the reflectivity reference or compensation body 2 into the urine sample. The function of the reflectivity reference or compensation piece 2 is described below.

In the schematic block diagram of FIG. 2 there is illustrated a spectral reflectivity measuring structure for measuring the spectral reflectivity of color reaction test papers, etc. Thus FIG. 2 shows a light source lamp 4, a collimator lens 5, and a condensing lens 6. A filter 7 between components 5 and 6 permits passage only of light of a predetermined wavelength from the white light emitted from the light source lamp 4. The light whose wavelength has been selected by the filter 7 is condensed by the condensing lens 6, travels approximately vertically onto the surfaces of the color reaction test paper body 1 and the reflectivity reference or compensation body 2, and then is reflected in the direction $2\pi$. A light detector 8 receives a part of the light reflected from the surface of the body 2 or the body 1 and transforms the received light into an electrical signal. While in the illustrated example there is shown a simplified structure receiving a part of the reflected light, it is preferable and possible to arrange an integration sphere type of optical system so as to cause the largest part of the $2\pi$—direction reflected light to be received by the light detector 8. In FIG. 2 there is also shown a first-stage amplifier 9 receiving the output from the detector 8, and the output of the amplifier 9 is connected with a sensitivity adjusting circuit 10 having a sensitivity adjusting knob 11 and connected with an ammeter 12, so that by turning the knob 11 it is possible to adjust the position of the pointer of the ammeter 12, the latter having a reflectivity scale ranging from 0% to 100%.

The above-described structure of FIGS. 1 and 2 is representative of a basic example of the present invention. This particular example operates as follows:

The color reaction test body 1 reacts selectively with one of the abnormal substances in the urine sample and provides a coloring having an intensity corresponding to the concentration of the abnormal substance in the urine. The individual who is carrying out the analysis observes this coloring and can detect therefrom the presence or absence of the abnormal substance. However, it is difficult in this way to know the concentration of the abnormal substance in the sample. Moreover, it is all the more difficult and almost impossible to determine the degree of coloring with the unaided-eye observation in the event that the urine specimen itself is intensely colored. The reason why this latter situation obtains is now described with reference to the spectral reflectivity characteristic curves shown in FIG. 3.

Referring to FIG. 3 the abscissa of the illustrated graph is plotted according to measured wavelength, while the ordinate is plotted according to relative reflectivity with the 100% reflection standard at each measured wavelength corresponding to that of the color reaction test paper piece 1 with pure water applied thereto. The curve A of FIG. 3 indicates the reflectivity characteristic of the color reaction test paper piece 1 which has reacted with an abnormal substance of a certain concentration in the case where the urine sample is itself of no particular color. The curve B indicates the reflectivity characteristic of the color reaction test paper piece 1 with a urine sample applied thereto which contains no abnormal substance but which on the other hand is itself colored with a given intensity. While the characteristic of the curve B varies with the cause and degree of the coloring, in many cases the curve B will at least partly overlap the curve A. Therefore, with a urine sample which contains an abnormal substance which is to be detected and which furthermore is itself colored to a given degree for one reason or another, the reflectivity characteristic of the color reaction test paper piece 1 is obtained as a result of combining the curves A and B, with the addition of these curves being indicated by the curve C. Thus, the examiner or individual carrying out the observation sees the overall reflected light spectrum indicated by the curve C, so that it is not possible for such an individual to normalize the result simply by way of unaided-eye observation of the extent of coloring.

The above problem is solved by way of the present invention in the following manner:

The examiner grasps the strip 3 and dips both the test body 1 and the reference body 2 into the urine sample so that the urine sample is uniformly applied to both bodies. Then, after these bodies are removed from the sample measurement is made with the test body 1 and the reference body 2 applied to the spectral reflectivity measuring means, or in other words the optical means of FIG. 2. First the reflectivity reference or compensation piece 2 is placed at the predetermined measuring position in the optical means of FIG. 2, so that the reflected light is received by the light detector 8. Now the sensitivity adjusting knob 11 is suitably turned by the operator so that the ammeter 12 gives an indication of 100%. After this latter adjustment has been carried out, the color reaction test body 1 is situated at the measuring position. Now the ammeter 12 will indicate the reflectivity of the color reaction test paper piece 1. It is apparent that this latter reflectivity is of a value having a ratio with respect to the reflectivity of the reference body 2 corresponding to 100%, and accordingly this particular value is related only to the color reaction of the color reaction test paper piece 1. Thus, the reflectivity reference or compensation body 2 performs the same function as that of a sample blank used in colorimetric analysis.

Figure 4:
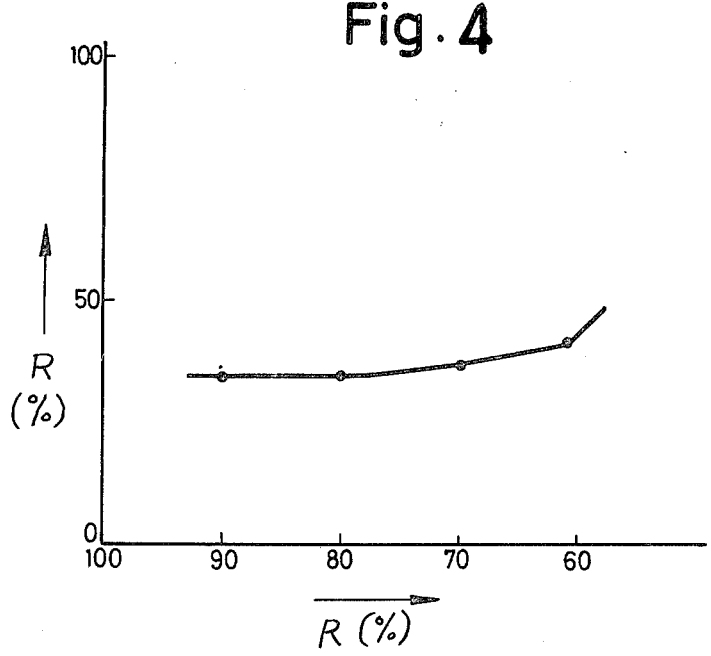
FIG. 4 is a graph illustrating relative reflectivity of color reaction test paper when utilizing the reflectivity compensation or reference piece according to one example of the present invention.

FIG. 4 illustrates the result of an experiment indicating that the above-mentioned operation can in practice be carried out. In this experiment a plurality of mock samples are utilized, these samples being made of urine containing corresponding abnormal substances but not being colored, with dye of various concentrations being added. A measuring wavelength is used which presents the most intense color reaction. The abscissa of the graph of FIG. 4 is plotted according to the relative reflectivity of the reflectivity reference body 2 with the mock samples applied thereto, with the standard value 100% of the reflectivity reference body 2 being the reflectivity thereof with pure water applied thereto. The ordinate of the graph of FIG. 4 is plotted according to the relative reflectivity of the color reaction test body 1 which is measured in the manner set forth above, but with respect to these mock samples. As is clearly apparent from FIG. 4, even if the reflectivity of the reference body 2 decreases by nearly 30% due to the coloring of the urine sample itself, the relative reflectivity of the color reaction test body 1 hardly changes. Therefore, according to the method of the present invention it is possible to carry out accurate measurement of abnormal substances in the tested liquid independently of the coloring of the urine samples themselves from causes other than the substance which is to be detected. The concentration of the abnormal substances can be obtained by previously obtaining the relation between the standard substance of known concentration and the relative reflectivity. There will be absolutely no erroneous judgment of the presence of the abnormal substance when there is no such abnormal substance in the urine. The above description relates to the operation and effect of one particular example of the present invention. Other modified examples of the present invention are possible, as described below:

In the above example of the present invention, the reference body 2 is made of filter paper which is also the very same material used for the test body 1. However, the material used may be of other types such as cloth, paste-like solid material, etc. It is only required that the materials utilized for the reference body 2 have water-absorbing characteristics and dyeing characteristics similar to those of the color reaction test paper piece 1. The result of course is perfect if a material of entirely the same characteristics is used for the reference body 2 and the test body 1, with the latter differing only in connection with the reagent which gives the color reaction. Thus, in the above example of the present invention the reference body 2 is made of the very same material as the color reaction test body 1. Ideally it is preferable to use a material impregnated with various impregnating agents of the color reaction test body 1 and lacking only the color reaction for the suspected substance but otherwise having all of the other characteristics of the color reaction test body 1.

It is easily possible to provide modified embodiments of the invention which will enable the operator to carry out examinations of a plurality of abnormal substances, so that the invention is not restricted in this respect. FIG. 5 shows one such modified example. Thus, referring to FIG. 5, there are illustrated therein a plurality of color reaction test bodies 1, 1', 1" which are in the form of the color reaction filter paper pieces and which respectively are provided with suitable reagents for giving predetermined color reactions when responding to the presence of substances such as, for example, glucose, protein, bilirubin, etc., with this embodiment also having the reference body 2 as described above. All of these bodies are carried by the common means 3. The device of FIG. 5 is operated in exactly the same way as that of FIG. 1, the only difference being that the device of FIG. 5 has the added advantage of being able to quickly carry out a plurality of different tests for a plurality of different substances in a single operation.

What is claimed is:

1. A device for testing a liquid for aiding in the detection of a substance in the liquid, comprising a pair of liquid-absorbent bodies one of which is a test body and the other of which is a reference body, said bodies being made of materials which have substantially identical characteristics with respect to the liquid to be tested for reacting therewith to be colored identically thereby and to have the same light-reflecting properties except that the material of said test body differs from that of said reference body in that the material of said test body is capable of giving a color indication of said substance, and means connected with said bodies for facilitating the dipping thereof into and the removal thereof from a liquid which is to be tested, whereby after thus removing the bodies from the liquid a comparison of the colors thereof will provide the desired information.

2. The device of claim 1 and wherein said test body is in the form of a color reaction test paper.

3. The device of claim 2 and wherein said reference body is identical with said test body except that said reference body is incapable of reacting with said substance if it is present in the liquid which is tested.

4. The device of claim 1 and wherein said means includes an elongated strip common to and carrying both of said bodies.

5. The device of claim 4 and wherein one of said bodies is adjacent an end of said strip while the other of said bodies is adjacent said one body.

6. The device of claim 1 and including a plurality of said test bodies all of which have characteristics with respect to the liquid to be tested which are substantially identical with those of said reference body with said test bodies differing from each other and from said reference body only in that said test bodies are respectively capable of giving color indications of a plurality of different substances, respectively, in the liquid which is tested, and said means being connected with all of said bodies for facilitating the dipping thereof into and the removal thereof from the liquid which is to be tested.

7. The device of claim 1 and including an optical means for giving an indication of the reflectivity of said bodies after removal thereof from the liquid which is tested, whereby the relative reflectivity of said bodies given by said optical means will provide a quantitative value for said substance if the latter is present in the liquid which is tested.

8. The device of claim 7 and wherein said optical means includes a meter capable of being manually set to a 100% value for the reflectivity of said reference body and for then providing a value directly giving a quantative indication of said substance from the reflectivity of said test body.

9. A method of testing a liquid such as urine, comprising steps of dipping into and removing from the liquid, in any sequence, a pair of liquid-absorbent bodies one of which is a test body for giving a color indication in connection with a substance in the liquid and the other of which is a reference body which has characteristics substantially identical with that of said test body except that said reference body is incapable of giving a color indication of the presence of said substance, and then determining a color difference, if any, between said bodies.

10. A method according to claim 9 and wherein a plurality of said test bodies for respectively providing indications of different substances in the liquid are dipped into and removed from the liquid and then compared with the reference body.

11. A method according to claim 9 and including the step of comparing the bodies with an optical means which has a meter capable of being manually adjusted to provide a percentage indication, and including the step of first adjusting the meter to provide a 100% indication in connection with the reference body and then reading the meter to determine the percentage indicated thereby in connection with the test body.

12. A method according to claim 9 and wherein the liquid which is tested is urine so that both of said bodies will be colored identically by said urine unless said urine contains said substance for providing said test body with a color different from that of said reference body.

* * * * *

UNITED STATES PATENT OFFICE
CERTIFICATE OF CORRECTION

PATENT NO. : 4,125,372
DATED : November 14, 1978
INVENTOR(S) : Shoji Kawai, et al.

It is certified that error appears in the above–identified patent and that said Letters Patent are hereby corrected as shown below:

[73] Assignee: Kabushiki Kaisha Kyoto Daiichi Kagaku, Japan

Signed and Sealed this

First Day of May 1979

[SEAL]

Attest:

RUTH C. MASON
*Attesting Officer*

DONALD W. BANNER
*Commissioner of Patents and Trademarks*